(12) United States Patent
Lin et al.

(10) Patent No.: US 9,700,890 B2
(45) Date of Patent: Jul. 11, 2017

(54) CENTRIFUGE/MAGNET-BASED ANALYZERS AND METHOD OF OPERATING THEREOF

(71) Applicant: Shaoxing PushKang Biotechnology Co., Ltd., Shaoxing, Zhejiang Province (CN)

(72) Inventors: Chia-Hui Lin, Schaoxing (CN); Yi-Feng Yang, Shaoxing (CN); Bo Yu, Shaoxing (CN)

(73) Assignee: SHAOXING PUSHKANG BIOTECHNOLOGY CO., LTD., Shaoxing, Zhejiang Province (CN)

( * ) Notice: Subject to any disclaimer, the term of this patent is extended or adjusted under 35 U.S.C. 154(b) by 153 days.

(21) Appl. No.: 14/621,378

(22) Filed: Feb. 12, 2015

(65) Prior Publication Data

US 2016/0121330 A1 May 5, 2016

(30) Foreign Application Priority Data

Oct. 31, 2014 (TW) .............................. 103137931 A (51) Int. Cl.
| | | |
|---|---|---|
| *C12N 13/00* | (2006.01) | |
| *B04B 5/10* | (2006.01) | |
| *B01L 3/00* | (2006.01) | |
| *G01N 33/543* | (2006.01) | |

(52) U.S. Cl.
CPC ..... *B01L 3/502723* (2013.01); *B01L 3/50273* (2013.01); *B01L 3/502753* (2013.01); *B01L 3/502761* (2013.01); *G01N 33/54333* (2013.01); *B01L 3/502738* (2013.01); *B01L 2200/0652* (2013.01); *B01L 2200/0684* (2013.01); *B01L 2300/0806* (2013.01); *B01L 2300/0864* (2013.01); *B01L 2300/0867* (2013.01); *B01L 2400/043* (2013.01); *B01L 2400/0409* (2013.01); *B01L 2400/0688* (2013.01)

(58) Field of Classification Search
CPC ....................... B01L 3/50276; B01L 3/502753
See application file for complete search history.

(56) References Cited

U.S. PATENT DOCUMENTS

2008/0035579 A1\* 2/2008 Lee .................. B01L 3/502761
210/695
2008/0108120 A1\* 5/2008 Cho .................. B01F 13/0059
435/173.7

\* cited by examiner

*Primary Examiner* — Kathryn Wright
(74) *Attorney, Agent, or Firm* — Cheng-Ju Chiang (57) ABSTRACT

The present invention provides centrifuge/magnet-based analyzers and methods of operating thereof. The analyzer comprises three discs sandwiched together, in which each disc has difference functions. The top disc comprises magnetic units configured in patterns, whereas the bottom disc comprises tracks and magnetic units free to move in the tracks. The magnetic field co-generated by the top disc and the bottom disc attracts the magnetic beads in the intermediate disc to move and thus facilitates the reactions in the intermediate disc.

10 Claims, 9 Drawing Sheets

CENTRIFUGE/MAGNET-BASED ANALYZERS AND METHOD OF OPERATING THEREOF

TECHNICAL FIELD

At least one embodiment of the present invention provides centrifuge/magnet-based analyzers and methods of operating thereof. More particularly, the methods are related to manipulation of the centrifugal force and regional magnetic field on the centrifuge/magnet-based analyzers by changing the rotational speed.

DESCRIPTION OF THE RELATED ART

Enzyme-linked immunosorbent assay (ELISA) is an assay which has been widely used to determine the presence of specific proteins in biochemistry. Based on the specific binding between an antibody and its antigen and the following color development, ELISA can also be applied as quantitative assays for chemical and biological molecules.

In 1972, Peter Perlmann and Eva Engvall published the first method to perform ELISA, which is famous in its high sensitivity. ELISA is popular in laboratories, especially in clinical levels, and one of the most well-known ELISA techniques is the "sandwich" ELISA. In a sandwich ELISA, the primary antibodies, antigens, horseradish peroxidase (HRP) labeled secondary antibodies, and substrates will be sequentially added to perform the test.

Conventional methods usually use 96-well microtiter plates to perform ELISA. Since each step in ELISA requires some incubation time and washing procedure, running ELISA consumes a lot of time on operating equipment and waiting for reactions to complete. And this is more acute when running ELISA on 96-well microtiter plates, because each well in the 96-well microtiter plates needs to be handled individually. Another disadvantage of conventional methods is that manual operations (e.g., using micropipette to load and distribute reagents) would lead to human errors and fatally affect the results.

In a sandwich ELISA, the primary antibodies are coated on the plate in advance. This indirect method of ELISA would dampen the binding efficiency of antibodies and therefore require more reagents and reaction time to complete a test. A sandwich ELISA, from coating primary antibodies to completing the tests, usually takes hours to days to finish. Moreover, more reagents and reaction time indicates that more non-specific binding would be induced.

In order to improve the defects by using 96-well microtiter plates, compact disc (CD) ELISA, a new technique featured in combining ELISA and centrifugal force, has been proposed. CD ELISA is a technique based on centrifugal force and discs similar to compact discs to perform ELISA. The discs used in CD ELISA are also known as chips, because they are coated with antibodies or antigens on the matrix and etched with multiple micro-channels, chambers, and microvalves on the surface.

A microvalve can trap fluid while the rotational speed of the disc is below the microvalve's burst frequency. If liquid is under a centrifugal force, the centrifugal force applied on the liquid will drive the liquid to move. But if the liquid moves to a microvalve, the microvalve will induce capillary pressure on the liquid-air interfaces to counteract with the centrifugal force and resist the liquid from moving through. Based on the counteraction between the centrifugal force and the capillary pressure, the liquid is trapped and stops moving while that the centrifugal force is no more than the capillary pressure. However, if the rotational speed is accelerated and the centrifugal force applied on the liquid is increased, the balance between the centrifugal force and the capillary pressure will finally be broken and the liquid will eventually surge through the microvalve. The rotational speed which broke down the balance between the centrifugal force and the capillary pressure at a microvalve is the burst frequency of the microvalve.

Users can inject several reagents into chambers on a disc in advance, and release the reagents sequentially and separately during an assay by controlling the rotational speed of the disc. Under different rotational speeds, different reagents will be release into an incubation chamber for reactions. In addition, CD ELISA requires a small amount of reagents but provide a high contact area for reactions, the reaction rate therefore can be significantly increased. Based on these advantages, CD ELISA can automatically complete the processes in few hours.

However, few disadvantages of CD ELISA have been identified. One is that the microvalves used in conventional CD ELISA are unstable, and one is that antibodies are hard to be uniformly coated on such micro-scale solid supports.

Each microvalve used in conventional CD ELISA has a burst frequency. This is one of the bases to sequentially and separately release reagents by controlling rotational speed. However, the burst frequency of a microvalve is fixed to a rough range instead of one specific rotational speed. Liquid usually surmounts a microvalve when the rotational speed is falling within the +/−20% range of the said burst frequency. Accordingly, if the burst frequencies of any two microvalves are close and the ranges are partially overlapping, reagents designed to be sequentially released may surmount the microvalves simultaneously and lead to failures.

Furthermore, coating antibodies on the solid support and binding antigens to the antibodies on a disc is difficult and unstable if the disc is in millimeter scale. The inconsistent distribution of antibodies and antigens among chambers, or even within one single chamber, will largely affect the results.

Some solutions have been proposed to improve the stability of microvalves. One of the solutions is wax plug, which is made of paraffin wax with a low melting point. The wax plug is to replace the microvalve to block microchannels. If a liquid trapped by a wax plug is going to be released into downstream chambers, laser will irradiate on that wax plug to open the microchannel. The technique using laser-controlled wax plugs provides a sophisticated mechanism to manipulate the release sequence of reagents and avoids the leakage often happened in conventional microvalves. However, discs using laser-controlled wax plugs are far from affordable. The discs require precise instrument to be fabricated and work.

Some other solutions have been proposed to improve the efficiency of antibody coating. One of the solutions is microsphere, which is mostly made of plastic or magnetic materials. The microspheres are covered with functional groups for conjugating with antibodies or antigens. The conjugated microspheres will be injected into chambers to interact with samples and reagents in an assay. But how to retain the injected microspheres in a chamber is a problem.

Conventionally, microchannels in micrometer scale are used to trap plastic microspheres in a chamber since that the microchannels allow fluid, but plastic beads, to pass through. However, fabricating such fine microchannels is costly. Some others provide an alternate solution, which is utilizing magnetic beads and magnetic field. The movement of magnetic beads can be controlled by magnetic field generated from an external source. The magnetic field attracts and keeps the magnetic beads in a chamber during incubation and reactions. However, the magnetic field is invariable and the movement of magnetic beads is stagnant in this technique.

Since the magnetic field is constantly fixed at a place, the reaction between the antibodies and sample would be less effective. Furthermore, magnetic beads are still retained ineffectively under the magnetic field.

SUMMARY

At least one embodiment of the present invention provides a centrifuge/magnet-based analyzer. More particularly, the centrifuge/magnet-based analyzers alter the centrifugal force and regional magnetic fields by changing the rotational speed to move the magnetic beads.

At least one embodiment of the present invention provides a centrifuge/magnet-based analyzer. The centrifuge/magnet-based analyzer comprises a first disc. There are multiple first magnetic units disposed on the first disc, in which the multiple first magnetic units are located on the same radius ring or different radius rings centered on the center of the first disc.

The centrifuge/magnet-based analyzer also comprises a second disc, in which the second disc is the main disc to conduct analysis. The second disc is configured below and adjacent to the first disc, but not directly contact with or attached to the first disc. The second disc comprises a first air vent, a first main chamber, a second air vent, a second main chamber, a third air vent, a third main chamber, a first microvalve, a second microvalve, third microvalves, and multiple reaction units.

More particularly, the first air vent is disposed at the center of the second disc. The first air vent is connected to the first main chamber while the first main chamber is further connected to the second main chamber via the first microvalve. The second main chamber, on the other hand, comprises the second air vent. Similarly, a third main chamber comprising the third air vent is connected to the second main chamber via the second microvalve. The third main chamber is further connected to the multiple reaction units via the third microvalves.

Each of the multiple reaction units comprises an entry, an incubation chamber, a sample chamber, a detection chamber, a waste chamber, a fourth microvalve, and a forth air valve. The entry is connected to the third microvalve and the incubation chamber respectively, and the incubation chamber is separately connected with the sample chamber and the detection chamber. Notably, the sample chamber is configured at top side of the incubation chamber while the detection chamber is configured at the bottom side of the incubation chamber. The detection chamber is further connected with the waste chamber via the fourth microvalve and the air vent is connected to the top side of the waste chamber.

The centrifuge/magnet-based analyzer also comprises a third disc, in which the third disc is configured below and attached with the second disc. More particularly, the third disc comprises multiple tracks. Each track in the third disc contains a second magnetic unit, and the second magnetic unit is free to move in the track accommodating thereof.

At least one embodiment of the present invention provides a method of operating centrifuge/magnet-based analyzers. The method begins with an injecting step, an affixing step, and a configuring step. More particularly, at least one reagent, magnetic beads, and the sample are injected into a second disc in the injecting step and the second disc is affixed to a third disc in affixing step. The third disc here comprises multiple tracks, in which each track accommodates a second magnetic unit. Furthermore, the at least one reagent here can be any solution based on analysis requirements. After the affixing step, the second disc and the third disc together are configured to a first disc in the configuring step, in which the first disc comprises multiple magnetic units.

The method further comprises a rotating step, a releasing step, and an obtaining step. In the rotating step, the rotational speed of the second disc is elevated to an incubation speed to mix and incubate. In the following releasing step, the rotational speed of the second disc is increased to at least one release speed. More particularly, the number of the at least one release speed is determined in accordance with the number of the at least one reagent. The at least one release speed is to selectively and sequentially release the at least one reagent. In the obtaining step, optical analysis is applied to obtain results while the rotational speed of the second disc is at an analyzing speed.

DESCRIPTION OF THE PREFERRED EMBODIMENTS

Figure 1:
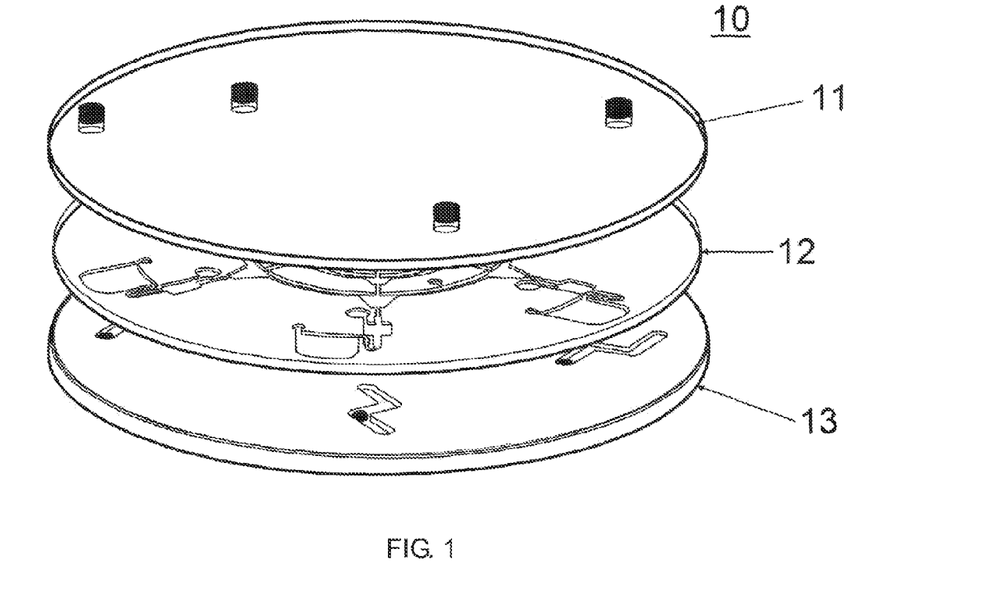
FIG. 1 illustrates a centrifuge/magnet-based analyzer, according to some embodiments of the present invention.

FIG. 1 illustrates a centrifuge/magnet-based analyzer, according to some embodiments of the present invention. As illustrated in FIG. 1, the centrifuge/magnet-based analyzer comprises three layers. From the top to the bottom, the three layers are a first disc 11, a second disc 12, and a third disc 13 respectively. Before performing an assay, the second disc 12 and the third disc 13 are attached together by, for example, using a pair of male fasteners and female fasteners. The second disc 12 and the third disc 13 are then mounted onto a centrifuge, which is a place adjacent to the first disc 11.

Figure 2:
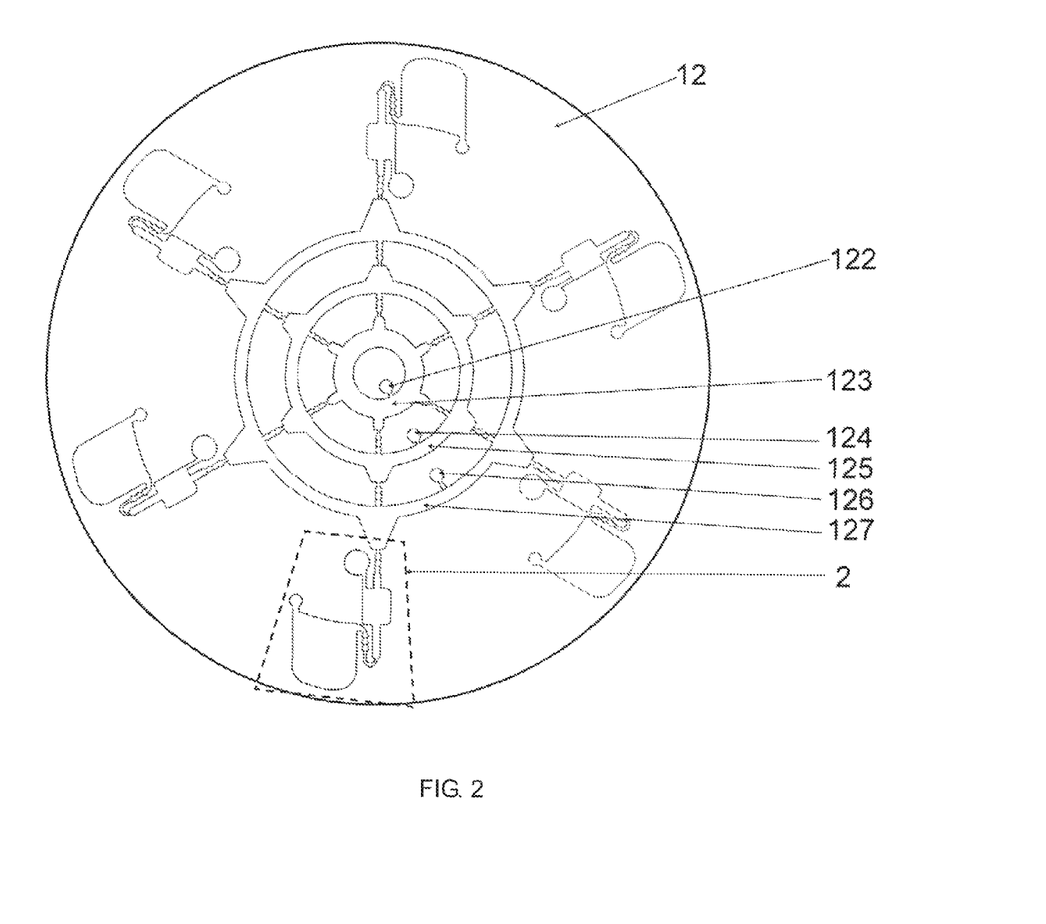
FIG. 2 illustrates a second disc, according to some embodiments of the present invention.
Figure 3:
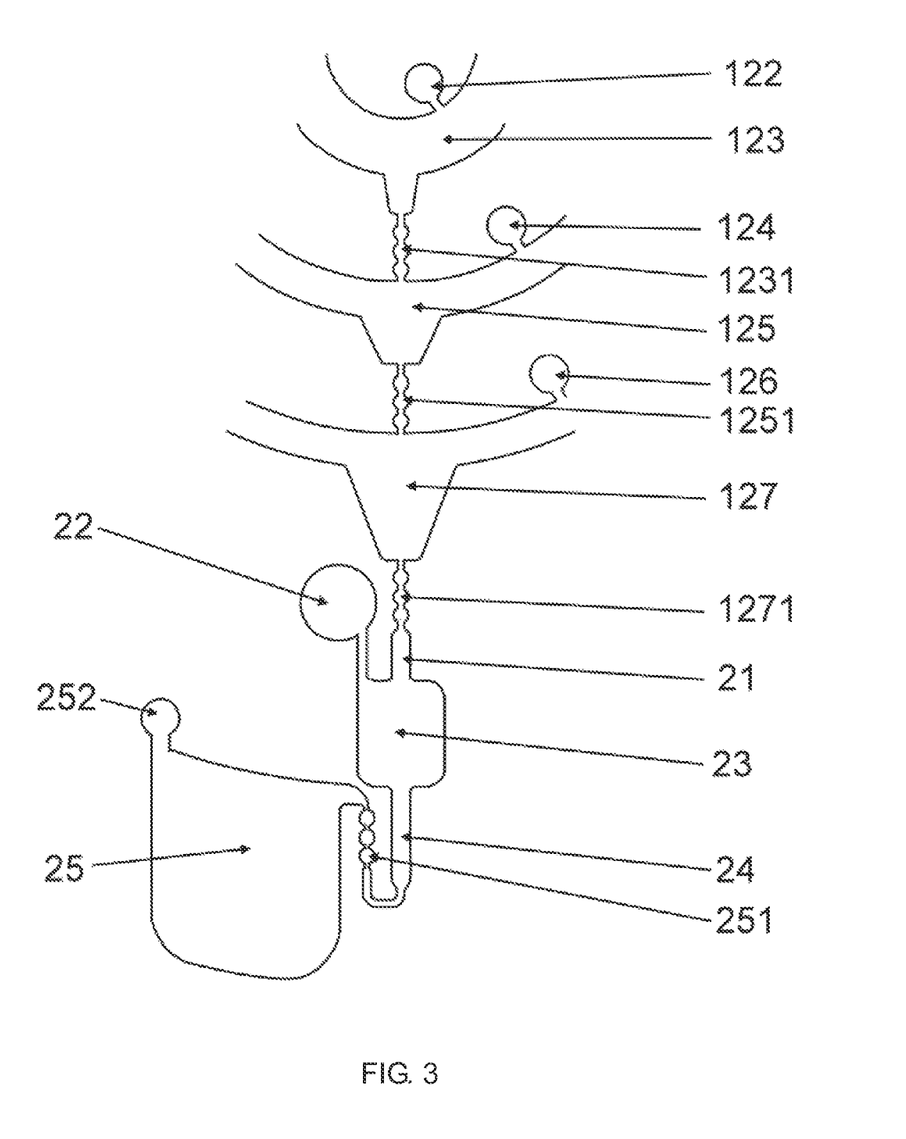
FIG. 3 illustrates a reaction unit, according to some embodiments of the present invention.

Referring to FIG. 2 and FIG. 3, FIG. 2 illustrates a second disc and FIG. 3 illustrates a reaction unit, according to some embodiments of the present invention. As illustrated in FIG. 2 and FIG. 3, a first air vent 122 is disposed at the center of the second disc 12. The first air vent 122 is connected to the first main chamber 123 while the first main chamber 123 is further connected to the second main chamber 125 via a first microvalve 1231. The second main chamber 125, on the other hand, comprises the second air vent 124. Similarly, a third main chamber 127 comprising a third air vent 126 is connected to the second main chamber 125 via the second microvalve 1251. The third main chamber 127 is further connected to multiple reaction units 2 via the third microvalve 1271.

In some embodiments, a first reagent, a second reagent, a third reagent are injected into the first main chamber 123, the second main chamber 125, and the third main chamber 126 respectively through the first air vent 122, the second air vent 124, and the third air vent 126. That is, the first air vent 122, the second air vent 124, and the third air vent 126 are not only used for ventilation but also used as injection ports.

In FIG. 2, the embodied disc comprises six reaction units 2. However, the number of the reaction units 2 is not limited to six. The number of the reaction units 2 is determined based in part on the analysis requirements. For example, the disc could be designed as, similar to convention microtiter plates, containing twenty-four reaction units or ninety-eight reaction units, which the number is a multiple of six.

In FIG. 3, the embodied reaction unit 2 is connecting with the third microvalve 1271. More particularly, an entry 21 is connected to the third microvalve, and an incubation chamber 23 is connected to the entry 21. The incubation chamber 23 is further connected with a sample chamber 22 and a detection chamber 24 separately. Notably, the sample chamber 22 is configured at top side of the incubation chamber 23 while the detection chamber 24 is configured at the bottom side of the incubation chamber 23. Furthermore, the detection chamber 24 is connected with a waste chamber 25 via the fourth microvalve 251 and a forth air vent 252 is connected to the top side of the waste chamber 25.

In some embodiments, the first microvalve 1231, the second microvalve 1251, the third microvalve 1271, and the fourth microvalve 1291 each is a string of hollow spheres connected together. However, in accordance with the analysis requirement, the first microvalve 1231, the second microvalve 1251, the third microvalve 1271 each can also be a fishbone-shaped microvalve or a twisted microchannel.

Figure 4:
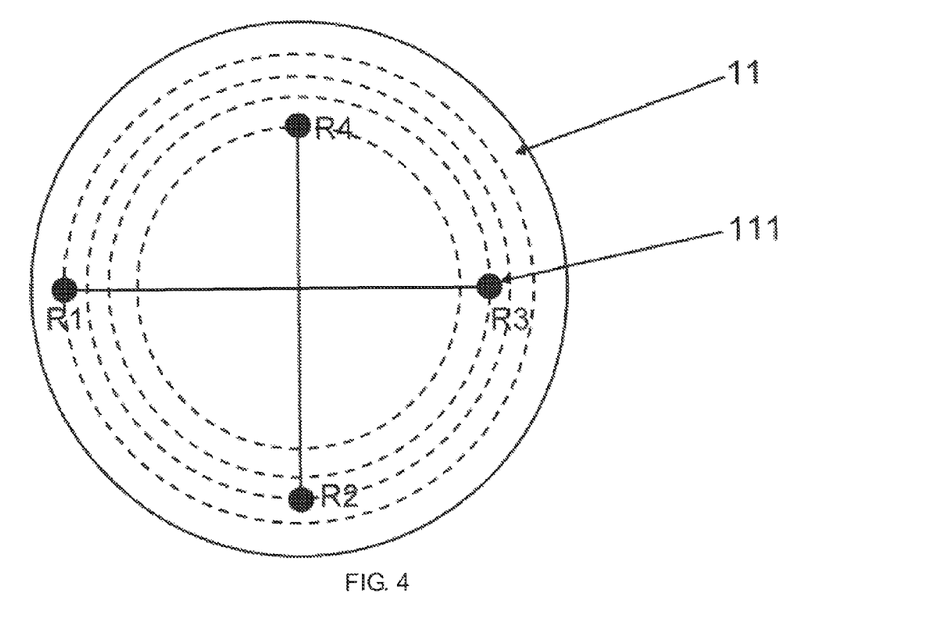
FIG. 4 illustrates the configuration of first magnetic units on a first disc, according to some embodiments of the present invention.

FIG. 4 illustrates the configuration of first magnetic units on a first disc, according to some embodiments of the present invention. On the exemplary first disc 11, four radius rings centered on the center of the first disc 11 were virtually drawn for further explanations. The four radius rings are in four different radii, in which the R1, R2, R3, and R4 in FIG. 4 denote the four radii respectively. And multiple first magnetic units 111 are disposed on the four radius rings respectively to provide a control mechanism to control the magnetic beads 3.

Figure 5:
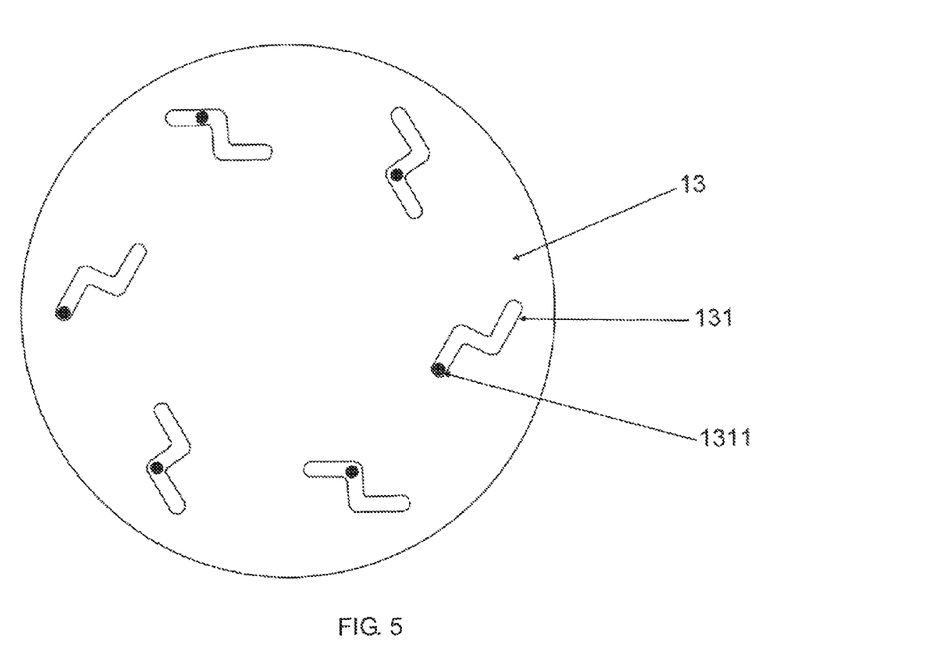
FIG. 5 illustrates a third disc, according to some embodiments of the present invention.

FIG. 5 illustrates a third disc, according to some embodiments of the present invention. As illustrated in FIG. 5, the third disc 13 comprises multiple tracks 131. The number of tracks in this exemplary third disc 13 is consistent with the number of reaction units in the exemplary first disc 11 in FIG. 2. Each track 131 is in zigzag and contains a second magnetic unit 1311, in which the second magnetic unit 1311 is free to move in the track 131 accommodating thereof. If the first disc 11, the second disc 12, and the third disc are configured together, the second magnetic units 1311 is able to move relatively to the first magnetic units 111 on the first disc 11 and affect the reaction in the reaction units 2 on the second disc 12. The first magnetic unit and the second magnetic unit 1311 each can be an electromagnet or a permanent magnet. Since permanent magnets do not require energy to be active, the first magnetic units and the second magnetic units in some embodiments both are permanent magnets.

The mechanism underlying the centrifuge/magnet-based analyzers will be further explained in the following embodiments. The embodiments of FIGS. 6A-6E are focusing on reaction units 2 performing ELISA. However, the present invention may be applied to devices and fields other than ELISA in some other embodiments.

Figure 6A:
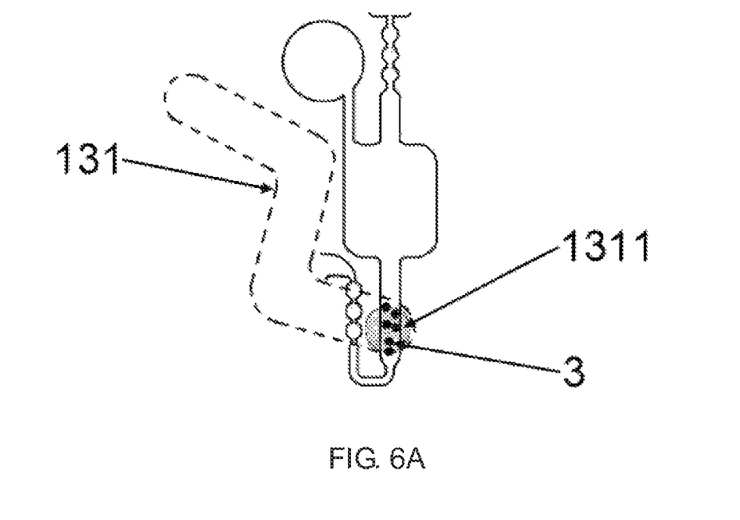
FIGS. 6A-6E illustrate the motion of magnetic beads, according to some embodiments of the present invention.
Figure 6B:
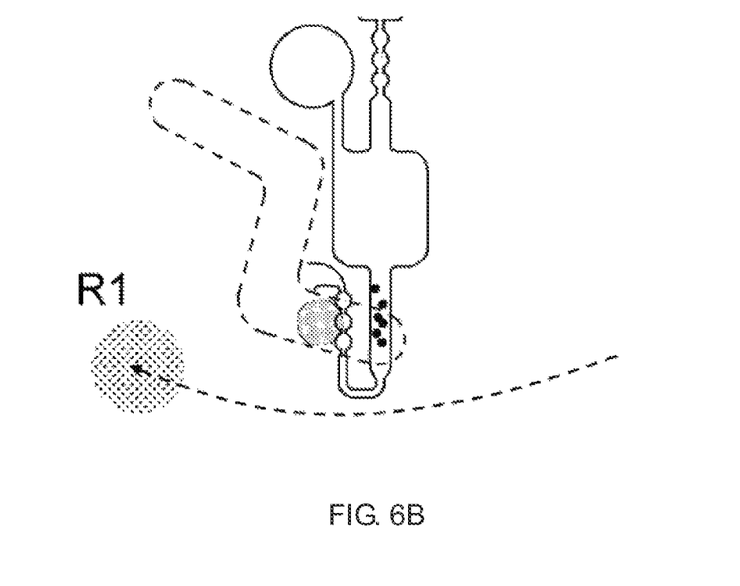
Figure 6C:
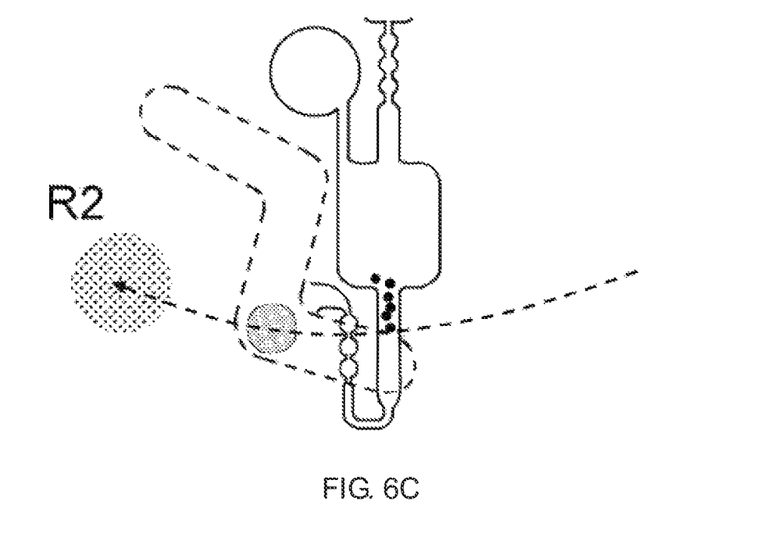
Figure 6D:
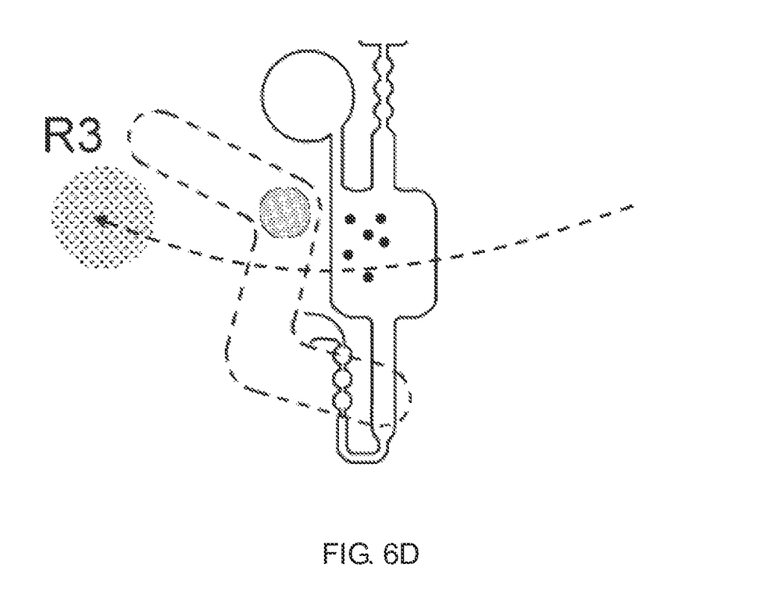
Figure 6E:
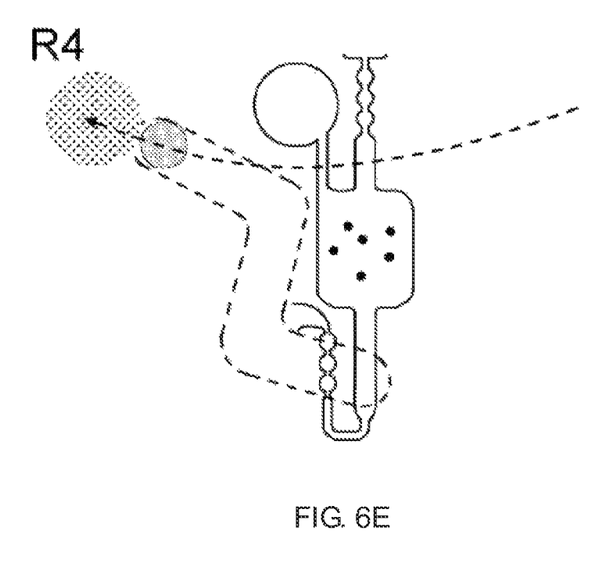

FIGS. 6A-6E illustrates the motion of magnetic beads, according to some embodiments of the present invention. FIG. 6A is a top view of the combination of the first disc 11, the second disc 12, and the third disc 13. In particular, the second disc 12 is attached to the third disc 13, and the second disc 12 and the third disc 13 together is placed adjacently to the first disc 11. The sample chamber 22 is used as an injection port for samples and reagents of ELISA, e.g. primary antibodies and HRP labeled secondary antibodies. In the embodiments of FIG. 6A, the sample chamber 22 is used for injecting magnetic beads 3 coated with antibodies or antigens.

After the magnetic beads 3, the sample, and the antibodies are injected, the second disc 12 will begins to spin to drive these fluid and magnetic beads 3 into a detection chamber 24. As the second disc is continuing to spin, the magnetic beads will be attracted by second magnetic units 1311 in tracks 131 of the third disc 13 and shuttle between the detection chamber 24 and the incubation chamber 23.

Since the second magnetic units 1311 are free to move, they will be attracted by the first magnetic beads 111 which are respectively located on the R1 ring, the R2 ring, the R3 ring, and the R4 ring on the first disc 11. As illustrated in FIG. 6B-6E, the magnetic beads 3 will be attracted indirectly by the first magnetic units 111 on the R1 ring, the R2 ring, the R3 ring, and the R4 ring while the second disc 12 is rotating relatively to the first disc 11.

In some late stages, the rotational speed of the second disc 12 will reach a threshold that the centrifugal force applied on the second magnetic units 1311 is greater than the magnetic force between the first magnetic units 111 and the second magnetic units 1311. And the second magnetic units 1311 will be spun down and stay at the position as illustrated in FIG. 6A. At the same time, the magnetic beads, attracting by the second magnetic units 1311, are kept in the detection chamber 24 instead of flowing into the waste chamber 25.

The method of operating the centrifuge/magnet-based analyzers will be explained in the following embodiments.

Figure 7:
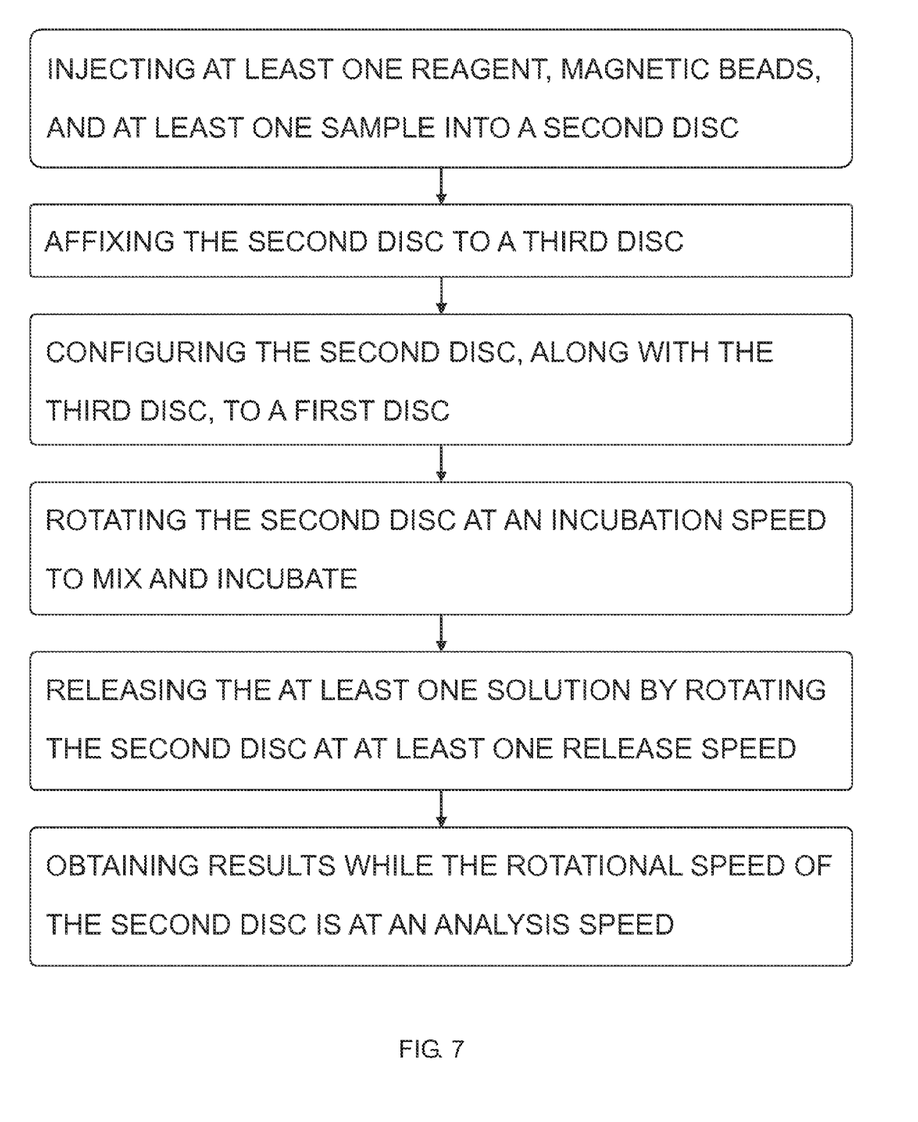
FIG. 7 is a flow diagram illustrating a method of operating centrifuge/magnet-based analyzers, according to some embodiments of the present invention.

FIG. 7 is a flow diagram illustrating a method of operating centrifuge/magnet-based analyzers, according to some embodiments of the present. As illustrated in FIG. 7, the method is initiated with injecting at least one reagent, magnetic beads 3, and at least one sample into a second disc 12. The second disc 12, then, is affixed to a third disc 13. In particular, the third disc 13 comprises multiple tracks 131 and each track 131 accommodates a second magnetic unit 1311.

The at least one reagent comprises a reagent I, a reagent II, and a reagent III in the embodiments. For ELISA, the reagent I here is the stop solution, the reagent II is the developing reagent, and the reagent III is the wash buffer.

In some embodiments, the reagent I (i.e., the stop solution) is injected into a first main chamber 123 through a first air vent 122, the reagent II (i.e., the developing reagent) is injected into a second main chamber 125 through a second air vent 124, and the reagent III (i.e., the wash buffer) is injected into a third main chamber 127 through a third air vent 126. Moreover, magnetic beads 3 (i.e., magnetic beads 3 conjugated with primary antibody), the secondary antibody (i.e., the secondary antibody conjugated with HRP), and the sample are injected into an incubation chamber 23 through a sample chamber 22.

As used in conventional ELISA, the wash buffer may be a PBS-T wash buffers comprising 0.05% Tween-20, and the developing reagent may be the substrates for the enzyme (e.g., the HRP enzyme) coupling with the primary antibody or even Coomassive Brillian Blues (e.g., Coomassie Brilliant Blue G-250). The stop solution may, depending on the assay, be strong acids (e.g., 2M $H_2SO_4$ and HCl) or strong bases (e.g., NaOH).

In the following step, the second disc 12, along with the third disc 13, is configured to a first disc 11, in which the first disc 11 comprises multiple first magnetic units 111. In particular, the second disc 12 and the third disc 13 is configured below the first disc 111 to induce the magnetic attraction between the second magnetic units 1311 in the third disc 13 and the first magnetic units 111 in the first disc 11. The distance between the first disc 11 and the second/third discs 12, 13 will determine the strength of the magnetic attraction, a user thus can adjust the distance between the discs in accordance with rotational speed used in an assay.

After the discs are configured together, the second disc 12 will be rotated at a spread speed, the first rotational speed, to spread the reagent I, the reagent II, the reagent III, the magnetic beads 3, the secondary antibody, and the sample. More particularly, the spread speed is under the burst frequencies of the first microvalve 1231, the second microvalve 1251, and the third microvalve 1271. Therefore, the reagent I, the reagent II, and the reagent III is spreading within the main chambers respectively during this stage. And the sample, the magnetic beads 3, and the secondary antibody are spreading into the incubation chamber 23 and the detection chamber 24.

After these elements for ELISA have been spread in the chambers respectively, the second disc 12 will be rotated at an incubation speed, the second rotational speed. Under the incubation speed, the magnetic attraction between the first magnetic units 111 and the second magnetic units 1311 is greater than the centrifugal force applied on the second magnetic units 1311. Because second magnetic units 1311 are relatively rotating to the first magnetic units 111, the second magnetic units 1311 will be attracted by different first magnetic units 111 and shuttle in the tracks 131 like illustrated in FIG. 6B-6E.

After the incubation stage, the second disc 12 will be rotated at at least one release speed. The number of the at least one release speed may be in accordance with the number of the at least one reagents. Therefore, the rotational speed of the second disc 12 will be increase from one level to another to selectively release some reagents in the disc, until all the reagent were released.

In the embodiments of FIG. 7, the reagent III is the first to release to perform the washing step, as in conventional ELISA. The rotational speed of the second disc 12 is first elevated to a level that the centrifugal force applied on the second magnetic units 1311 is greater than the magnetic force. Under this stage, the second magnetic units 1311 will be spun down to the end of the tracks 131, a distal region from the center of the third disc 13. At the same time, the magnetic beads 3 are attracted and kept in the detection chamber 24 of the reaction unit 2 of the second disc 12, whereas the reagents and sample are flowing into a waste chamber 25 of the reaction unit 2 of the second disc 12.

After that, the second disc 12 will be rotated at one of the at least one release speed. At this rotational speed, the centrifugal force applied on the second magnetic units 1311 is greater than the magnetic force, and most the antibodies and the sample will be in the waste chamber 25. Besides, the reagent III in the third main chamber 127 will surmount the third microvalve 1271 and flow into the detection chamber 24 of the reaction unit 2 to perform the washing step.

After the washing step, the second disc 12 will be further rotated at another of the at least one release speed. At this rotational speed, the centrifugal force applied on the second magnetic units 1311 is greater than the magnetic force, and the reagent III will flow into the waste chamber 25. Besides, the reagent II in the second main chamber 125 will surmount the second microvalve 1251 and the third microvalve 1271 and flow into the detection chamber 24 of the reaction unit 2 to develop colors.

Similar to the incubating step, the developing step may also utilize the magnetic beads 3 to facilitate the reaction. The second disc 12 will be rotated at a developing speed, which is another rotational speed. Under the developing speed, the magnetic attraction between the first magnetic units 131 and the second magnetic units 1311 is, again, greater than the centrifugal force applied on the second magnetic units 1311. And the second magnetic units 1311 will attract the magnetic beads 3 to shuttle between the incubation chamber 23 and the detection chamber 24 to facilitate the color development.

After the developing step, the second disc 12 will be rotated at still another of the at least one release speed. At this rotational speed, the centrifugal force applied on the second magnetic units 1311 is greater than the magnetic force, and the reagent I in the first main chamber 123 will surmount the first microvalve 1231, the second microvalve 1251, and the third microvalve 1271 and flow into the detection chamber 24 of the reaction unit 2 to inactive reactions and generate end products.

In the embodiments of FIG. 7, the release speeds for the reagent I, the reagent II, and the reagent III are different, and each is greater than another. That is, the release speed for the reagent I is greater than that of the reagent II, while the release speed for the reagent II is greater than that of the reagent III.

In the analyzing step, the second disc 12 will be rotated at an analysis speed, which is yet another rotational speed, while under the detection of a spectrophotometer. The spectrophotometer is used to obtain the optical density of each end product.

The embodiments of FIG. 7 are used to explain the underlying mechanism of the centrifuge/magnet-based analyzers. Though the following embodiments are also based on ELISA and the second disc 12 and the third disc 13 in FIG. 7 are collectively referred to as the "combined discs" therein, it should be obvious that the application of the centrifuge/magnet-based analyzers is not limit to ELISA.

The first experiment was conducted to determine the concentration of human chorionic gonadotropin (hCG) in samples. Similar to FIG. 7, the magnetic beads 3 conjugated with the primary antibody, the secondary antibody, and six samples were injected into the sample chamber 22. The six samples are products of a serial dilution, which is originated from a known source. The concentration of each sample is listed in Table 1.

TABLE 1

| | Sample A | Sample B | Sample C | Sample D | Sample E | Sample F |
|---|---|---|---|---|---|---|
| hCG (mIU/mL) | 0 | 10 | 20 | 50 | 100 | 250 |

In particular, the volume of the magnetic beads 3 is 15 µL and the secondary antibody is 20 µL. Furthermore, 120 µL of the stop solution, 240 µL of the developing reagent, and 1200 µL of the wash buffer were injected into the first main chamber 123, the second main chamber 125, and the third main chamber 127 via the first air vent 122, the second air vent 124, and the third air vent 126 respectively.

The combined discs were then rotated at 1200 RPM, the first release speed in this case, to transfer the wash buffer into the detection chamber 24 for reactions. The volume of the wash buffer in each reaction unit 2 was 200 µL since the wash buffer had been evenly distributed into six reaction units 2 on the combined disc. After then, the wash buffer in each reaction unit 2 rinsed the detection chamber 24 and flowed into the waste chamber 25. Notably, the magnetic beads 3 were kept in the detection chamber 24 by the attraction from the second magnetic units 1311 under the first release speed.

The combined discs were further rotated at 2400 RPM, the second release speed in this case, to transfer the developing reagent into the detection chamber 24 for reactions. The volume of the developing reagent in each reaction unit 2 was 40 µL since the developing reagent had been evenly distributed into six reaction units 2 on the combined disc. After then, the developing reagent in each reaction unit 2 developed colors in the detection chamber 24 and flowed into the waste chamber 25. Notably, the magnetic beads 3 were kept in the detection chamber 24 by the attraction from the second magnetic units 1311 under the second release speed.

Figure 8:
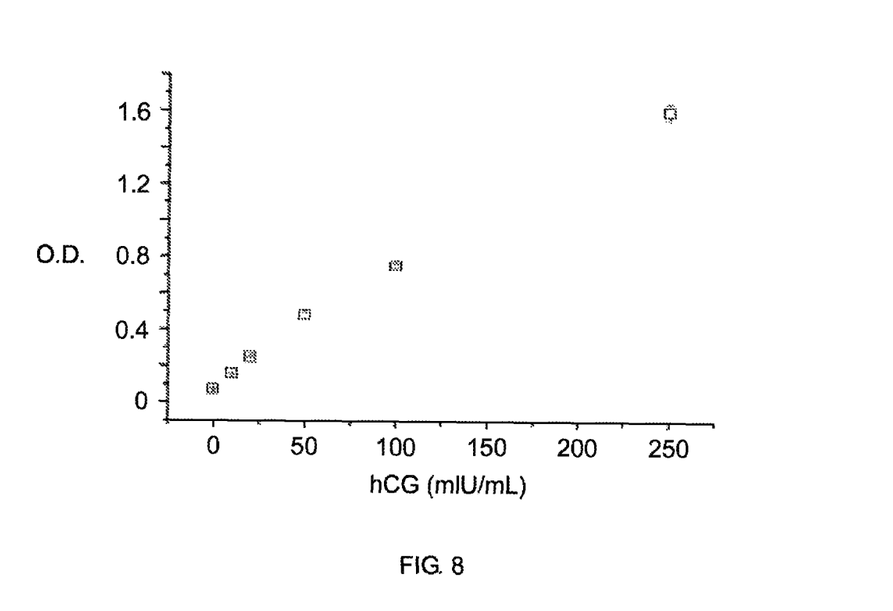
FIG. 8 is a graph illustrating the result of quantitative hCG testing performed with some embodiments of the present invention.

The combined discs were then rotated at 3600 RPM, the third release speed in this case, to transfer the stop solution into the detection chamber 24 for reactions. The volume of the stop solution in each reaction unit 2 was 20 µL since the stop solution had been evenly distributed into six reaction units 2 on the combined disc. After then, the stop solution flowed into the waste chamber 25. Notably, the magnetic beads 3 were kept in the detection chamber 24 by the attraction from the second magnetic units 1311. The result of this quantitative hCG testing is shown in FIG. 8. According to FIG. 8, the correlation coefficient of the result is about 0.997, which confirms that the embodied centrifuge/magnet-based analyzer used in the first experiment is highly accurate and sensitive.

The second experiment was conducted to determine the concentration of CA-125, also known as cancer antigen 125, in samples. Similar to FIG. 7, the magnetic beads 3 conjugated with the primary antibody, the secondary antibody, and six samples were injected into the sample chamber 22. The six samples, each is 15 µL in volume, are products of a serial dilution, which is originated from a known source. The concentration of each sample is listed in Table 2.

TABLE 2

| | Sample G | Sample H | Sample I | Sample J | Sample K | Sample L |
|---|---|---|---|---|---|---|
| CA-125 (mIU/mL) | 0 | 25 | 50 | 100 | 200 | 400 |

In particular, the volume of the magnetic beads 3 is 35 µL and the secondary antibody is 30 µL. Furthermore, 360 µL of the stop solution, 480 µL of the developing reagent, and 960 µL of the wash buffer were all injected into the first main chamber 123, the second main chamber 125, and the third main chamber 127 via the first air vent 122, the second air vent 124, and the third air vent 126 respectively.

The combined discs were first rotated at 800 RPM, the incubation speed in this case, to transfer the samples, the magnetic beads 3, and the secondary antibody to the incubation chamber 23 and the detection chamber 24. The magnetic beads 3 were shuttling in a way similar to that in the first experiment.

The combined discs were then rotated at 1700 RPM to transfer the wash buffer into the detection chamber 24 for reactions. The volume of the wash buffer in each reaction unit 2 was 160 µL since the wash buffer had been evenly distributed into six reaction units 2. After then, the wash buffer in each reaction unit 2 flowed into the waste chamber 25. Notably, the magnetic beads 3 were kept in the detection chamber 24 by the attraction from the second magnetic units 1311 under the first release speed.

The combined discs were further rotated at 2800 RPM to transfer the developing reagent into the detection chamber 24 for reactions. The volume of the developing reagent in each reaction unit 2 was 80 µL since the developing reagent had been evenly distributed into six reaction units 2. After then, the developing reagent in each reaction unit 2 developed colors in the detection chamber 24 and flowed into the waste chamber 25. Notably, the magnetic beads 3 were kept in the detection chamber 24 by the attraction from the second magnetic units 1311 under the second release speed.

The combined discs were then rotated at 4100 RPM, the last release speed in this case, to transfer the stop solution into the detection chamber 24 for reactions. The volume of the stop solution in each reaction unit 2 was 60 µL since the stop solution had been evenly distributed into six reaction units 2. After then, the stop solution flowed into the waste chamber 25. Notably, the magnetic beads 3 were kept in the detection chamber 24 by the attraction from the second magnetic units 1311.

Figure 9:
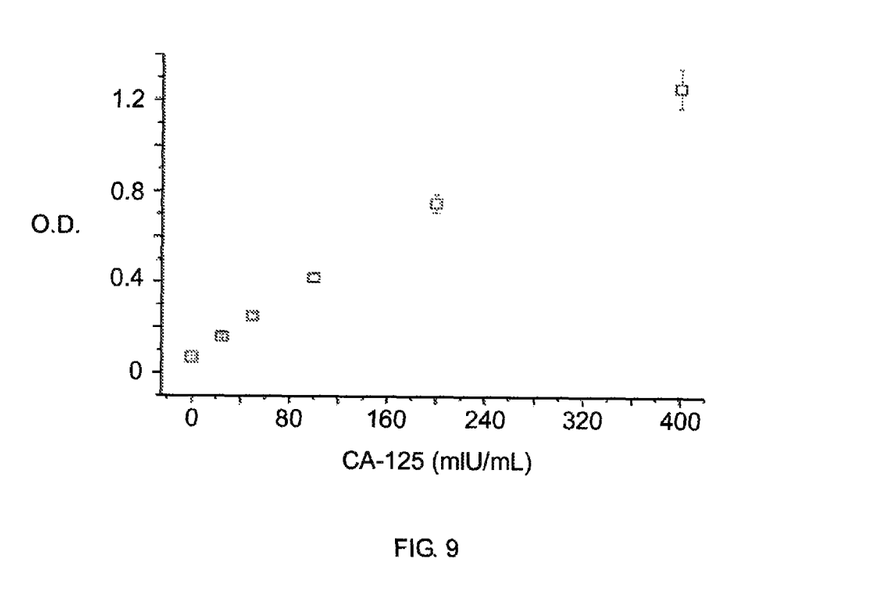
FIG. 9 is a graph illustrating the result of CA-125 level testing performed with some embodiments of the present invention.

The result of this quantitative CA-125 testing is shown in FIG. 9. According to FIG. 9, the correlation coefficient of the result is about 0.993, which confirms that the embodied centrifuge/magnet-based analyzer used in the second experiment is high accurate and sensitive.

Some embodiments of the present invention have potential in the point-of-care testing (POCT) industry. POCT devices are characterized in fast analysis process and high portability. POCT devices promise a future allowing healthcare providers in poorly equipped clinics to perform diagnostic tests locally. The POCT technology will soon become an important part to improve global health.

There are many inventions described and illustrated above. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

What is claimed is:
1. A centrifuge/magnet-based analyzer, comprising:
   a first disc, comprising multiple first magnetic units,
   wherein the multiple first magnetic units are located on the same radius ring or different radius rings centered on the center of the first disc;

a second disc, configured below the first disc, comprising:
  a first air vent, disposed at the center of the second disc;
  a first main chamber, connected with the first air vent, wherein the first main chamber is an annular space of the second disc;
  a second main chamber, comprising a second air vent, wherein the second main chamber is connected to the first main chamber via multiple first microvalves, wherein the second main chamber is an annular space and the first main chamber is surrounded by the second main chamber; and
  a third main chamber, comprising a third air vent, wherein the third main chamber is connected to the second main chamber via multiple second microvalves, wherein the third main chamber is an annular space and the second main chamber is surrounded by the third main chamber;
  multiple reaction units, wherein each reaction unit is connected to the third chamber via a third microvalve, and wherein each reaction unit comprises:
  an entry, connected to the third microvalve;
  an incubation chamber, connected to the entry;
  a sample chamber, connected to the incubation chamber;
  a detection chamber, connected to the incubation chamber;
  a waste chamber, connected to the detection chamber via a fourth microvalve; and
  a forth air valve, connected to the waste chamber; and
a third disc, configured below and attached to the second disc, comprising multiple tracks, wherein each track accommodates a second magnetic unit, and wherein the second magnetic unit is movable;
wherein the number of the multiple reaction units is equal to the number of the multiple tracks;
a spectrophotometer, analyzing the product which is in the detection chamber.

2. The analyzer according to claim 1, wherein the number of the multiple reaction units is a multiple of 6.

3. The analyzer according to claim 1, wherein the multiple first magnetic units and the second magnetic unit are permanent magnets.

4. The analyzer according to claim 1, wherein the first microvalve, the second microvalve, the third microvalve, and the fourth microvalve each is a string of hollow spheres.

5. The analyzer according to claim 1, wherein each track is a zigzag track.

6. A method for operating centrifuge/magnet-based analyzers, comprising:

providing the centrifuge/magnet-based analyzer as claimed in claim 1;
injecting at least three reagents, magnetic beads, and at least one sample into the second disc, wherein the at least three reagents are injected into the first main chamber, the second chamber, and the third chamber respectively;
affixing the second disc to the third disc;
configuring the second disc, along with the third disc, to the first disc;
rotating the second disc at an incubation speed;
releasing the at least three reagents, comprising the substeps of:
  increasing the rotational speed of the second disc to a first release speed to release one of the at least three reagents in the first main chamber;
  increasing the rotational speed of the second disc to a second release speed to release one of the at least three reagents in the second main chamber, wherein the second release speed is higher than the first release speed; and
  increasing the rotational speed of the second disc to a third release speed to release one of the at least three reagents in the third main chamber, wherein the third release speed is higher than the second release speed;
  wherein the rotational speed of the incubation speed is slower than the first release speed;
obtaining results by optical analysis.

7. The method according to claim 6, wherein the at least one reagent comprises a wash buffer, and wherein the wash buffer is released into the incubation chamber and the detection chamber in the releasing step.

8. The method according to claim 6, wherein the at least one reagent comprises a developing reagent, and wherein the developing reagent is released into the incubation chamber and the detection chamber in the releasing step to develop colors.

9. The method according to claim 6, wherein the at least one reagent comprises a stop solution, and wherein the stop solution is released into the incubation chamber and the detection chamber in the releasing step to terminate reactions and generate end products.

10. The method according to claim 6, wherein the distance between the center of the second disc and the first main chamber is smaller than the distance between the center of the second disc and the second main chamber, and wherein the distance between the center of the second disc and the second main chamber is smaller than the distance between the center of the second disc and the third main chamber.

\* \* \* \* \*